Figure 1:
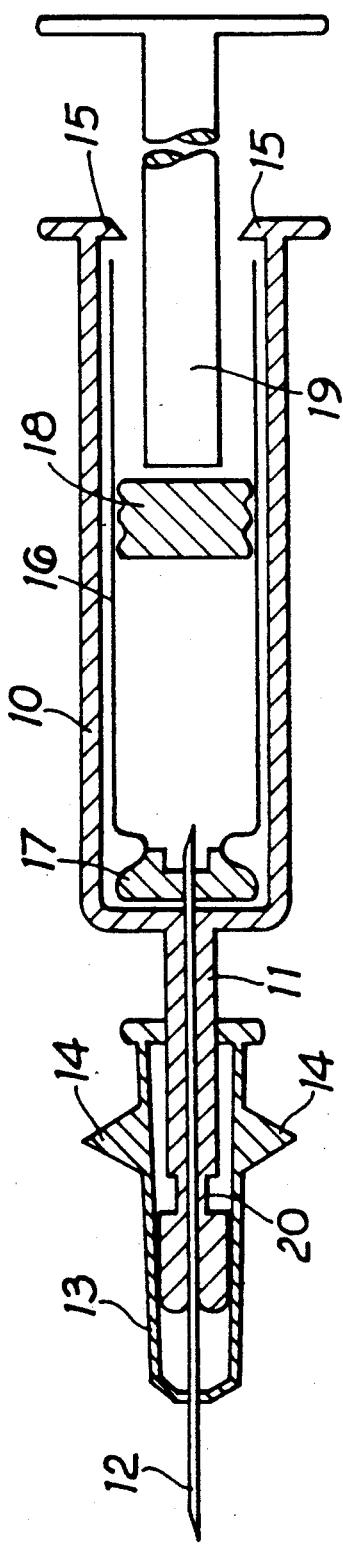

United States Patent [19]

Byrne et al.

[11] Patent Number: 4,990,141
[45] Date of Patent: Feb. 5, 1991

[54] SINGLE-USE SYRINGE

[75] Inventors: Phillip O. Byrne; Penelope R. Sisson; Harry R. Ingham, all of Newcastle upon Tyne, England

[73] Assignee: National Research Development Corporation, London, England

[21] Appl. No.: 294,786

[22] Filed: Jan. 9, 1989

[30] Foreign Application Priority Data

Jan. 15, 1988 [GB] United Kingdom ............... 8800883

[51] Int. Cl.⁵ ........................ A61M 5/32; A61M 5/00
[52] U.S. Cl. .................................... 604/198; 604/232
[58] Field of Search ............... 604/110, 192, 197, 198, 604/232, 233, 234, 235, 263, 220, 218; 128/765

[56] References Cited

U.S. PATENT DOCUMENTS

| 3,811,441 | 5/1974 | Sarnoff | 604/234 |
|---|---|---|---|
| 3,895,633 | 7/1975 | Bartner et al. | 604/232 |
| 4,221,218 | 9/1980 | Pfleger | 604/218 |
| 4,252,118 | 2/1981 | Richard et al. | 604/110 |
| 4,391,272 | 7/1983 | Staempfli | 604/110 |
| 4,583,978 | 4/1986 | Porat et al. | 604/218 |
| 4,650,468 | 3/1987 | Jennings, Jr. | 604/110 |
| 4,693,706 | 9/1987 | Ennis, III | 604/220 |
| 4,702,738 | 10/1987 | Spencer | 604/198 |
| 4,723,945 | 2/1988 | Theiling | 604/232 |
| 4,731,068 | 3/1988 | Hesse | 604/218 |
| 4,752,290 | 6/1988 | Schramm | 604/198 |
| 4,758,232 | 7/1988 | Chak | 604/220 |
| 4,801,295 | 1/1989 | Spencer | 604/110 |
| 4,804,372 | 2/1989 | Laico et al. | 604/263 |
| 4,820,272 | 4/1989 | Palmer | 604/110 |
| 4,850,994 | 7/1989 | Zerbst et al. | 604/198 |

FOREIGN PATENT DOCUMENTS

| 2258375 | 5/1974 | Fed. Rep. of Germany | 604/218 |
|---|---|---|---|
| 0219009 | 12/1924 | United Kingdom | 604/128 |
| 1150980 | 5/1969 | United Kingdom | 604/110 |
| 2187961 | 9/1987 | United Kingdom | 604/218 |
| 2197792 | 6/1988 | United Kingdom | 604/110 |
| 8900432 | 1/1989 | World Int. Prop. O. | 604/110 |

Primary Examiner—C. Fred Rosenbaum
Assistant Examiner—Sharon Rose
Attorney, Agent, or Firm—Cushman, Darby & Cushman

[57] ABSTRACT

A syringe which is suitable for discarding after a single use takes the form of a generally tubular syringe body which has a double-ended hollow needle extending generally axially through a first, closed end of the body and is open at its second end to permit insertion of a liquid container such as an ampoule containing a liquid material to be injected. A removable plunger rod is provided to enter such a container within the syringe body to inject liquid from it via the needle, and one or more resilient projections extend generally radially inwardly from the open end of the syringe body, to allow insertion of a liquid container but prevent its subsequent withdrawal.

6 Claims, 1 Drawing Sheet

U.S. Patent
Feb. 5, 1991
4,990,141

SINGLE-USE SYRINGE

The present invention is a syringe of a type intended for disposal after it has been used to deliver a single injection.

A range of syringes have been developed over recent years in which one or more parts of the syringe assembly are designed to be discarded after use. Thus the hypodermic needle itself, usually contained within a protective sheath or guard, may alone be discarded or the syringe assembly overall may be formed of a relatively cheap material allowing its complete disposal after a single use.

The original purpose of such developments was to obviate the need to clean and resterilise such equipment and thus, to avoid the danger of inadequately resterilised devices inadvertently being used on subsequent patients. However, more recently, it has been recognised that medical syringes discarded after legitimate use may be retrieved for subsequent illicit use, for example for self-injection by drug users. The emphasis has therefore switched from designing syringes which are merely disposable to producing syringes of which subsequent re-use is positively prevented.

One approach to designing a non-reusable syringe has been to devise a syringe in which the plunger is captured within the syringe barrel after use, so that withdrawal of the plunger in order to refill the syringe is made very difficult. See, for example, UK Patent Specification No. 2184657. However, such an approach has not been adapted for syringes of the type which are designed to receive a pre-filled ampoule containing the material to be injected. In addition, this approach entails discarding the plunger with the syringe.

It is an object of the present invention to provide a syringe of the ampoule-loaded type which may safely be discarded after a single use without any significant risk of illicit re use.

The syringe according to the present invention comprises a generally tubular syringe body which is closed at a first end thereof, a double-ended hollow needle extending through said closed end generally axially with respect to the syringe body, the second end of said syringe body being generally open so as to permit the insertion of a liquid container into said syringe body, a resilient retaining means extending from said second end of said syringe body in a generally radially inward direction so as to allow the insertion of a said liquid container but to prevent its removal by engaging the adjacent end of a said container, and a plunger rod adapted to reversibly enter a said container within said syringe body.

Liquid containers conventionally used in hypodermic injection syringes take the form of tubular ampoules, closed at one end by a cap which can be pierced by the inward end of a double-ended needle and closed at the other end by a bung which is slidable within the ampoule to expel its contents via the needle. The syringe according to the invention is designed to receive such conventional ampoules without the need to modify the ampoules in any way. Thus, the plunger rod may freely abut the bung within such an ampoule to enable the liquid to be injected into a patient, but may then be withdrawn before the syringe and ampoule are discarded. If desired, the plunger rod may be removably attachable to the adjacent end of the syringe body, in the manner of a dental injection syringe handle.

The double-ended needle may be irreversibly attached to the syringe body before use but it is preferred that the needle be incorporated in the syringe body, during the manufacture of the latter, for example by molding the syringe body around the needle. Preferably, the syringe is provided with a sheath for the needle, slidably mounted for movement between a first position in which the needle is exposed for use and a second position in which the needle is enclosed therein. It is preferred that the sheath be retained in said second position in a manner which renders subsequent re-exposure of the needle very difficult. Such a slidable sheath may be mounted upon the syringe body but in a particularly preferred form of the invention, the needle is disposed within an axial projection extending from the closed end of the syringe body and the sheath is slidably mounted upon that projection.

At the open end of the syringe body, a resilient retaining means extends in a generally radially inward direction. The resilient retaining means may take the form of one or more inwardly projecting spigots. Such a spigot may, in one embodiment of the invention, be an annular web. Preferably such spigot(s) is/are shaped so as to assist their deflection when an ampoule is inserted in the syringe body but to abut the adjacent end of the ampoule once it has been inserted. For example the axially outer face thereof may be inclined while the inner face may be flat in a radial direction.

Figure 2:
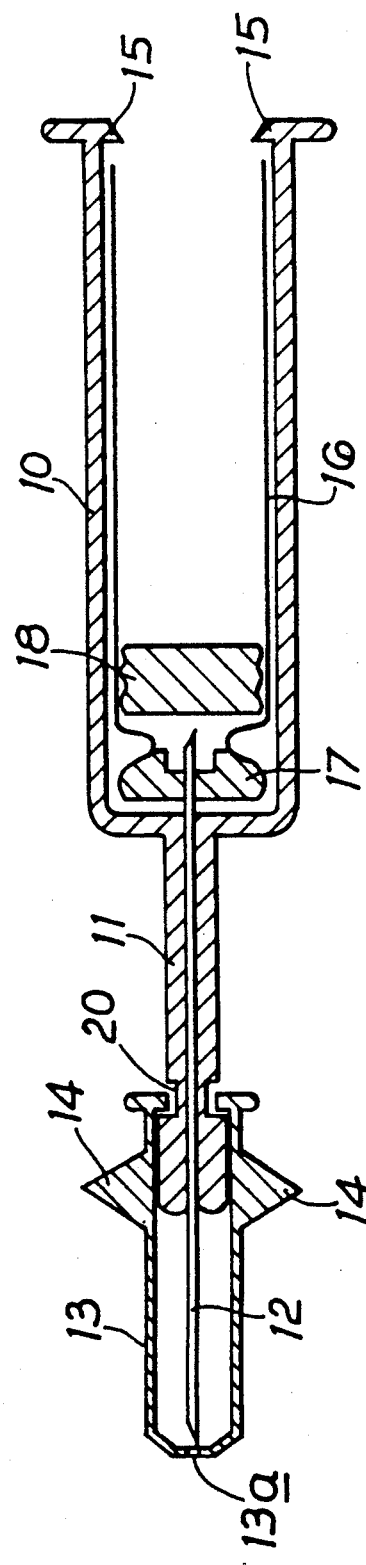

The invention will now be further described with reference to the accompanying drawings, wherein FIG. 1 is an axial sectional view of one preferred embodiment of the single-use syringe according to the present invention, with an ampoule inserted therein, in a condition of use; and FIG. 2 is a view corresponding to FIG. 1, showing the syringe in a condition for disposal.

The illustrated syringe comprises a generally cylindrical barrel 10, closed at one end thereof. The barrel 10 is molded in a synthetic polymeric material and has, formed integral therewith and projecting from its closed end, an axial extension 11. A double-ended hypodermic needle 12 extends axially through the extension 11. A hollow sheath 13 is a sliding push-fit upon the extension 11 and has an aperture 13a in its closed end, through which the needle 12 is able to project when the sheath is in its inward position illustrated in FIG. 1. The sheath 13 has a pair of lateral projections 14 to assist movement of the sheath over the length of the extension 11.

At its open end, the syringe barrel 10 is formed with a pair of resilient, inwardly projecting spigots 15, which reduce the effective minimum diameter of the open end to slightly less than that of a conventional ampoule 16. The spigots 15 have an inclined outer face and a flat inner face and are readily deflected when the ampoule 16 is being inserted in the barrel 10, but when the spigots return to their natural position, they project inwardly beyond the open end of the ampoule such that their flat inner faces prevent its withdrawal from the barrel 10. The inward end of the ampoule 16 is closed by a cap 17 which is readily pierced by the adjacent end of the needle 12 when the ampoule is first inserted in the barrel 10.

In use, the ampoule 16 is loaded into the barrel until the cap 17 is pierced and the spigots 15 have resumed the illustrated position. The bung 18, which as usual in such ampoules is slidable within the ampoule 16, may then be pushed further into the ampoule 16 by means of a plunger rod 19, which is inserted in the open end of the barrel 10 and abuts the bung 18. In this way, the liquid within the ampoule is expressed through the needle and an injection may be carried out in the usual manner.

When the injection has been completed, the plunger rod 19 is removed and the bung 18 remains in the position shown in FIG. 2. The ampoule is retained within the syringe barrel by the spigots 15. The sheath 13 is now slid along the extension 11 until its inward end nests in an annular slot 20 in the extension. The slot 20 retains the sheath against retraction and in this position, as illustrated in FIG. 2, the sheath completely encloses the previously exposed end of the needle 12. The syringe assembly as illustrated may now be safely discarded, without any serious risk of its illicit reuse.

We claim:

1. A hypodermic syringe suitable for safe disposal after a single use, which syringe comprises:
   (a) a generally tubular syringe body which is closed at a first end thereof;
   (b) an elongated projection extending in an axial direction from said closed first end of the generally tubular syringe body;
   (c) a double-ended hollow needle extending generally axially through said elongated projection from the interior of the syringe body to beyond the distal end of the projection;
   (d) a needle sheath slidably mounted upon said elongated projection for movement between a first position in which the needle is exposed for use and a second position in which the needle is enclosed therein;
   (e) the second end of said syringe body being generally open whereby an ampoule may be inserted into said syringe body;
   (f) an ampoule having a generally tubular body, a closure member at a first end thereof and a piston slidable within the generally tubular body;
   (g) a resilient retaining means extending from said second end of said syringe body in a direction which is generally radially inward with respect to said syringe body, whereby to allow said ampoule to enter said syringe body but to obstruct and thereby prevent removal of said ampoule; and
   (h) a plunger rod which is adapted to enter a said ampoule within said syringe body and to engage the piston of said ampoule without interconnection therewith and thereby to slide the piston within the ampoule towards the closed end of said ampoule.

2. A hypodermic syringe according to claim 1, wherein said resilient retaining means is in the form of at least one spigot projecting from the second end of the syringe body towards the axial center of said syringe body.

3. A hypodermic syringe according to claim 2, wherein said at least one spigot is shaped to assist deflection thereof by said ampoule entering said syringe body but to abut the adjacent end of said ampoule within said syringe body.

4. A hypodermic syringe according to claim 3, wherein said spigot is in the form of an annular web.

5. A syringe suitable for discarding after a single use for use with an ampoule which has a generally tubular body, a closure member at a first end thereof and a piston slidable within the generally tubular body from a second end thereof, said syringe comprising:

a generally tubular syringe body which is closed at a first end thereof;

a double-ended hollow needle extending through said closed end generally axially with respect to the syringe body, a second end of said syringe body being generally open whereby to permit the insertion of said ampoule into said syringe body;

a resilient retaining means extending from said second end of said syringe body in a generally radially inward direction whereby to allow the insertion of said ampoule but to prevent its withdrawal by engaging the adjacent end of said ampoule; and a plunger rod adapted to enter said ampoule within said syringe body and to engage the piston of said ampoule without interconnection therewith, whereby to slide the piston within the ampoule.

6. A syringe according to claim 5, further comprising a needle sheath slidably mounted upon an axial projection extending from the closed end of the syringe body, for movement of said sheath between a first position in which the needle is exposed for use and a second position in which the needle is enclosed therein and the sheath is secured to said axial projection whereby to prevent re-exposure of the needle.

* * * * *